United States Patent
Olson et al.

(10) Patent No.: US 11,753,467 B2
(45) Date of Patent: Sep. 12, 2023

(54) ANTI-TIM3 MONOCLONAL ANTIBODIES AND CHIMERIC ANTIGEN RECEPTORS

(71) Applicant: NantBio, Inc., Culver City, CA (US)

(72) Inventors: Clifford Anders Olson, Culver City, CA (US); Kayvan Niazi, Culver City, CA (US); Hermes J. Garban, Culver City, CA (US); Raymond Wong, Los Angeles, CA (US); Shiho Tanaka, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 0 days.

(21) Appl. No.: 17/587,546

(22) Filed: Jan. 28, 2022

(65) Prior Publication Data

US 2022/0235130 A1 Jul. 28, 2022

Related U.S. Application Data

(60) Provisional application No. 63/142,777, filed on Jan. 28, 2021.

(51) Int. Cl.
| | |
|---|---|
| *C07K 16/28* | (2006.01) |
| *A61K 47/68* | (2017.01) |
| *C07K 14/725* | (2006.01) |
| *C07K 14/54* | (2006.01) |
| *C07K 14/715* | (2006.01) |

(52) U.S. Cl.
CPC ...... *C07K 16/2803* (2013.01); *A61K 47/6849* (2017.08); *C07K 14/5443* (2013.01); *C07K 14/7051* (2013.01); *C07K 14/7155* (2013.01); *C07K 2317/56* (2013.01); *C07K 2319/30* (2013.01)

(58) Field of Classification Search
CPC ............ C07K 16/2803; C07K 14/5443; C07K 14/7051; C07K 14/7155; C07K 2317/56; C07K 2319/30; A61K 47/6849
See application file for complete search history.

(56) References Cited

FOREIGN PATENT DOCUMENTS

| | | |
|---|---|---|
| EP | 3 585 403 A1 | 1/2020 |
| WO | 2016/068803 A1 | 5/2016 |
| WO | 2016/144803 A8 | 11/2016 |
| WO | 2017/205721 A1 | 11/2017 |
| WO | 2018/156434 A1 | 8/2018 |
| WO | 2019/140229 A1 | 7/2019 |
| WO | 2019/143607 A1 | 7/2019 |
| WO | WO-2019143607 A1 * | 7/2019 ......... A61K 39/3955 |

OTHER PUBLICATIONS

Ngiow et al., "Anti-TIM3 Antibody Promotes T Cell IFN-g-Mediated Antitumor Immunity and Suppresses Established Tumors", Cancer Research, Microenvironment and Immunology, vol. 71, No. 10, May 15, 2011, pp. 3540-3551.
Ngiow et al., "Prospects for TIM3-Targeted Antitumor Immunotherapy", Cancer Research, Review, vol. 71, No. 21, Nov. 1, 2011, pp. 6567-6571.
Extended European Search Report received for EP Patent Application Serial No. 22152774.0 dated Oct. 6, 2022, 9 pages.
Hosseinkhani et al., "Immune Checkpoints and CAR-T Cells: The Pioneers in Future Cancer Therapies?", International Journal of Molecular Sciences, vol. 21, No. 21, Article 8305, Nov. 5, 2020, pp. 1-26.
He et al., "Bispecific and split Car T cells targeting CD13 and TIM3 eradicate acute myeloid leukemia", Blood vol. 135, No. 10, Mar. 5, 2020, pp. 713-723.
Qin et al., "Novel immune checkpoint targets: moving beyond PD-1 and CTLA-4", Molecular, vol. 18, No. 1, Nov. 6, 2019, pp. 1-14.

* cited by examiner

*Primary Examiner* — Adam Weidner
*Assistant Examiner* — Laura Ann Essex
(74) *Attorney, Agent, or Firm* — Martin Fessenmaier; Umberg Zipser LLP

(57) ABSTRACT

Antibodies, fragments thereof, and chimeric proteins comprising same are presented that have specific binding activity against T-cell immunoglobulin mucin receptor 3 (TIM3). Advantageously, contemplated molecules can be used in pharmaceutical compositions for immune therapy, particularly in individuals receiving cancer vaccines and/or checkpoint inhibitor treatment.

20 Claims, No Drawings
Specification includes a Sequence Listing.

ANTI-TIM3 MONOCLONAL ANTIBODIES AND CHIMERIC ANTIGEN RECEPTORS

This application claims priority to our U.S. Provisional Patent application Ser. No. 63/142,777, which was filed Jan. 28, 2021, and which is incorporated by reference in its entirety.

SEQUENCE LISTING

The content of the ASCII text file of the sequence listing named 102719.003PRO_REV002_ST25.txt, which is 55KB in size, created on Jan. 11, 2021 and which is electronically submitted via EFS-Web along with the present application is incorporated by reference in its entirety.

FIELD OF THE INVENTION

The field of the invention is target specific binding molecules, especially as it relates to antibodies and chimeric antigen receptors, and derivatives thereof with binding specificity against T-cell immunoglobulin mucin receptor 3 (TIM3).

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The T-cell immunoglobulin mucin receptor 3 (TIM3) is a cell surface receptor that is implicated in modulating innate and adaptive immune responses and is generally known to exert inhibiting functions. However, some reports have also suggested stimulating functions, which may be influenced by the cellular context and/or the respective ligand. Most typically, TIM3 regulates macrophage activation, inhibits T-helper type 1 lymphocyte (Th1)-mediated auto- and alloimmune responses, and promotes immunological tolerance. TIM3 function is also strongly influenced by the type of cell in which it is expressed. For example, in CD8+ cells, TIM3 attenuates TCR-induced signaling, specifically by blocking NF-kappaB and NFAT promoter activities, resulting in the loss of IL-2 secretion. Expressed on Treg cells, TIM3 can inhibit Th17 cell responses. Expressed on dendritic cells (DCs), TIM3 positively regulates innate immune response and in synergy with Toll-like receptors promotes secretion of TNF-alpha. On the other hand, in tumor-infiltrating DCs, TIM3 suppresses nucleic acid-mediated innate immune response by interaction with HMGB1 and interfering with nucleic acid-sensing and trafficking of nucleic acids to endosomes.

Increasing recognition of the role of TIM3 lead to the development of various TIM3 targeting molecules. For example, WO 2019/140229 and WO 2016/144803 teach specific anti-TIM3 antibodies, and selected treatment methods using anti-TIM3 antibodies are described in WO2019143607A1. In other examples, as described in EP 3585403, chimeric antigen receptor (CAR) polypeptides were expressed in immune effector cells, such as T cells or Natural Killer (NK) cells and used in adoptive cell transfer to target and kill TIM3-expressing cancers. Further studies reported that anti-TIM3 antibodies promoted T cell IFN-γ-mediated antitumor immunity and suppressed established tumors as is discussed in *Cancer Res*. 2011 May 15;71(10): 3540-51; doi: 10.1158/0008-5472, and prospects for TIM3-targeted antitumor immunotherapy are discussed in *Cancer Res*. 2011 Nov. 1;71(21):6567-71. doi: 10.1158/0008-547. While such compositions and methods advantageously open at least some TIM3-specific therapeutic approaches, the number and avidity of TIM3 binder is relatively limited.

Thus, even though various systems and methods of TIM3 targeting are known in the art, all or almost all of them suffer from several drawbacks. Therefore, there remains a need for compositions and methods for new and improved TIM3 specific therapeutic and diagnostic molecules.

SUMMARY OF THE INVENTION

The inventive subject matter is directed to various compositions and methods of TIM3 specific therapeutic and diagnostic molecules and their use in diagnosis and treatment of an individual.

In one aspect of the inventive subject matter, the inventors contemplate an isolated antibody or fragment thereof, wherein the antibody or fragment thereof binds to T-cell immunoglobulin mucin receptor 3 (TIM3) and includes a variable heavy chain (VH) domain and a variable light chain (VL) domain, wherein the VH domain is selected form the group consisting of SEQ ID NO:1, SEQ ID NO:3, SEQ ID NO:5, SEQ ID NO:7, SEQ ID NO:9, and SEQ ID NO:11, and wherein the VL domain is selected form the group consisting of SEQ ID NO:2, SEQ ID NO:4, SEQ ID NO:6, SEQ ID NO:8, SEQ ID NO:10, and SEQ ID NO:12.

In one embodiment, the antibody or fragment comprises VH64-6 (SEQ ID NO:1) and VL64-6 (SEQ ID NO:2), optionally coupled together by a linker to form an scFv. In another embodiment, the antibody or fragment comprises VH64-15 (SEQ ID NO:3) and VL64-15 (SEQ ID NO:4), optionally coupled together by a linker to form an scFv. In a further embodiment, the antibody or fragment comprises VH64-31 (SEQ ID NO:5) and VL64-31 (SEQ ID NO:6), optionally coupled together by a linker to form an scFv. In a still further embodiment, the antibody or fragment comprises VH64-32 (SEQ ID NO:7) and VL64-32 (SEQ ID NO:8), optionally coupled together by a linker to form an scFv. In yet another embodiment, the antibody or fragment comprises VH64-39 (SEQ ID NO:9) and VL64-39 (SEQ ID NO:10), optionally coupled together by a linker to form an scFv. In a further embodiment, antibody or fragment comprises VH66-6 (SEQ ID NO:11) and VL66-6 (SEQ ID NO:12), optionally coupled together by a linker to form an scFv.

Most typically, but not necessarily, antibody is an IgG1 antibody or an scFv, and/or may further include a therapeutic agent (e.g., a chemotherapeutic drug, a radionuclide, or an immune stimulant such as a cytokine, a cytokine analog, a chemokine, or a checkpoint inhibitor). Alternatively, or additionally, the antibody or fragment may also comprise a detectable label.

In other embodiments, the inventors also contemplate a chimeric protein that comprises the antibody or fragment presented herein. For example, the chimeric protein may form a chimeric antigen receptor (CAR), which may have a CD3zeta (CD3ζ) or Fc receptor epsilon (FcεRIγ) signaling domain, or that may have one or more of a CD28 signaling domain, a 4-1BB signaling domain, and a CD3zeta (CD3ζ) signaling domain. Most typically, the CAR may have a CD8 hinge domain and a CD28 transmembrane domain. As will be readily appreciated, the CAR will be a recombinant CAR that is expressed in and presented on the surface of an NK cell or a cytotoxic T cell. In other examples, the chimeric protein may form a bispecific fusion protein (e.g., comprising an IgG Fc portion, and optionally further comprising at least one of an IL15α receptor portion, an IL15 portion, and an IL15 superagonist portion) or may form a bispecific killer cell engager (BiKE) or a trispecific killer cell engager (TriKe).

Therefore, the inventors also contemplate a recombinant nucleic acid that encodes the isolated antibody or fragment, or the chimeric protein presented herein. For example, the nucleic acid may be part of an expression vector or part of a recombinant viral genome or may be in form of a linear DNA. On the other hand, the recombinant nucleic acid may also be an RNA.

Viewed from a different perspective, the inventors also contemplate a pharmaceutical composition that includes a pharmaceutically acceptable carrier in combination with the isolated antibody or fragment or the chimeric protein as presented herein. Similarly, the inventors also contemplate a pharmaceutical composition that includes a pharmaceutically acceptable carrier in combination with the recombinant nucleic acid as presented herein.

In another aspect of the inventive subject matter, the inventors also a method of treating an individual, in which the pharmaceutical compositions presented herein are administered to the individual, typically to thereby reduce immune suppression in the individual. Most typically, the individual is being treated with a cancer vaccine and/or a checkpoint inhibitor. Therefore, the inventors also contemplate the use of the pharmaceutical compositions as presented herein in the treatment of cancer in an individual.

Various objects, features, aspects and advantages of the inventive subject matter will become more apparent from the following detailed description of preferred embodiments.

DETAILED DESCRIPTION

The inventors have discovered various anti-TIM3 antibodies that have high affinity and specificity with respect to binding to TIM3. In particularly preferred aspects, contemplated antibodies are human $IgG_1$ antibodies that have the $V_H$ and $V_L$ domains as shown below. However, it should be appreciated that the sequences presented herein can vary to at least some degree and may therefore have one or more amino acid substitutions, insertions, and/or deletions as is discussed in more detail below. Most typically, but not necessarily, $V_H$ and $V_L$ domains, or heavy and light chains with the same preceding numeral (e.g., 64-6) will be present in a TIM3 binding construct. However, other TIM3 binding constructs may only have the $V_H$ or $V_L$ domain, or a $V_H$ and a $V_L$ domain with non-identical preceding numeral. Moreover, TIM3 binding constructs may include those that have at least some of the CDRs (e.g., at least those from $V_H$ domain) as listed below.

```
64-6 VH domain amino acid sequence:
                                                         (SEQ ID NO: 1)
EVQLVESGGGLVQPGGSLRLSCAASGFTFSRYAMHWVRQAPGKGLEWVSAI

SGSGGYTYYADSVKGRFTISRDNSKNTLYLQMNSLRAEDTAVYYCARDRHWVLSA

FDVWGQGTLVTVSS 64-6 VL domain amino acid sequence:
                                                         (SEQ ID NO: 2)
DIQMTQSPSSLSASVGDRVTITCQASQDISNYLNWYQQKPGKAPKWYDASN

LETGVPSRFSGSGSGTDFTFTISSLQPEDIATYYCQQYDTFPFTFGQGTKVEIK 64-15 VH domain amino acid sequence:
                                                         (SEQ ID NO: 3)
EVQLVESGGGLVQPGGSLRLSCAASGFTFSSYYMHWVRQAPGKGLEWVSGI

SGSGGSTYYADSVKGRFTISRDNSKNTLYLQMNSLRAEDTAVYYCARGRGAWPFTR

VVAFDVWGQGTLVTVSS 64-15 VL domain amino acid sequence:
                                                         (SEQ ID NO: 4)
DIQMTQSPSSLSASVGDRVTITCQASQDISNYLNWYQQKPGKAPKWYDASN

LETGVPSRFSGSGSGTDFTFTISSLQPEDIATYYCQQWTALPLTFGQGTKVEIK 64-31 VH domain amino acid sequence:
                                                         (SEQ ID NO: 5)
MEVQLVESGGGLVQPGGSLRLSCAASGFTFSAYAMHWVRQAPGKGLEWVS

AINGNGGRTYYADSVKGRFTISRDNSKNTLYLQMNSLRAEDTAVYYCARDLTRTVP

FAFDVWGQGTLVTVSS 64-31 VL domain amino acid sequence:
                                                         (SEQ ID NO: 6)
DIQMTQSPSSLSASVGDRVTITCQASQDISNYLNWYQQKPGKAPKWYDASN

LETGVPSRFSGSGSGTDFTFTISSLQPEDIATYYCQQATGWPFTFGQGTKVEIK
```

-continued 64-32 VH domain amino acid sequence:
(SEQ ID NO: 7)
MEVQLVESGGGLVQPGGSLRLSCAASGFTFSKYAMHWVRQAPGKGLEWVS

AISGSGGYTYYADSVKGRFTISRDNSKNTLYLQMNSLRAEDTAVYYCARDLDFRIVG

FDVWGQGTLVTVSS 64-32 VL domain amino acid sequence:
(SEQ ID NO: 8)
DIQMTQSPSSLSASVGDRVTITCQASQDISNYLNWYQQKPGKAPKWYDASN

LETGVPSRFSGSGSGTDFTFTISSLQPEDIATYYCQQFNTVPLTFGQGTKVEIK 64-39 VH domain amino acid sequence:
(SEQ ID NO: 9)
MEVQLVESGGGLVQPGGSLRLSCAASGFTFSRYAMHWVRQAPGKGLEWVS

GISGSGGGTYYADSVKGRFTISRDNSKNTLYLQMNSLRAEDTAVYYCARDLDYRVS

GFDVWGQGTLVTVSS 64-39 VL domain amino acid sequence:
(SEQ ID NO: 10)
DIQMTQSPSSLSASVGDRVTITCQASQDISNYLNWYQQKPGKAPKWYDASN

LETGVPSRFSGSGSGTDFTFTISSLQPEDIATYYCQQFYSVPLTFGQGTKVEIK 66-6 VH domain amino acid sequence:
(SEQ ID NO: 11)
MEVQLVESGGGLVQPGGSLRLSCAASGFTFSKYAMHWVRQAPGKGLEWVS

AISGSGGSTYYADSVKGRFTISRDNSKNTLYLQMNSLRAEDTAVYYCARDLDYRFSG

FDVWGQGTLVTVSS 66-6 VL domain amino acid sequence:
(SEQ ID NO: 12)
DIQMTQSPSSLSASVGDRVTITCQASQDISNYLNWYQQKPGKAPKWYDASN

LETGVPSRFSGSGSGTDFTFTISSLQPEDIATYYCQQFAAIPLTFGQGTKVEIK

As will be readily appreciated, the binding specificity of the $V_H$ and $V_L$ domains is dictated by their respective CDR regions, and Table 1 below shows the amino acid sequences for the CDRs in the $V_H$ and $V_L$ domains. Therefore, based on the known CDR sequences, it is contemplated that antibodies and fragments thereof can be prepared that bind TIM3 and that include at least some of the CDRs of SEQ ID Nos: 25-60.

TABLE 1

| Clone | CDR-H1 | CDRH-2 | CDR-H3 | CDR-L1 | CDR-L2 | CDR-L3 |
|---|---|---|---|---|---|---|
| 64-6 | SRYAMH SEQ ID NO: 25 | AISGSGGYTY SEQ ID NO: 26 | DRHWVLSAFDV SEQ ID NO: 27 | QASQDISNYLN SEQ ID NO: 28 | DASNLET SEQ ID NO: 29 | QQYDTFPFT SEQ ID NO: 30 |
| 64-15 | SSYYMH SEQ ID NO: 31 | GISGSGGSTY SEQ ID NO: 32 | CARGRGAWPFT RVVAFDV SEQ ID NO: 33 | QASQDISNYLN SEQ ID NO: 34 | DASNLET SEQ ID NO: 35 | QQWTALPLT SEQ ID NO: 36 |
| 64-31 | SAYAMH SEQ ID NO: 37 | AINGNGGRTY SEQ ID NO: 38 | DLTRTVPFAFDV SEQ ID NO: 39 | QASQDISNYLN SEQ ID NO: 40 | DASNLET SEQ ID NO: 41 | QQATGWPFT SEQ ID NO: 42 |
| 64-32 | SKYAMH SEQ ID NO: 43 | AISGSGGYTY SEQ ID NO: 44 | DLDFRIVGFDV SEQ ID NO: 45 | QASQDISNYLN SEQ ID NO: 46 | DASNLET SEQ ID NO: 47 | QQFNTVPLT SEQ ID NO: 48 |
| 64-39 | SRYAMH SEQ ID NO: 49 | GISGSGGGTY SEQ ID NO: 50 | DLDYRVSGFDV SEQ ID NO: 51 | QASQDISNYLN SEQ ID NO: 52 | DASNLET SEQ ID NO: 53 | QQFYSVPLT SEQ ID NO: 54 |
| 66-6 | SKYAMH SEQ ID NO: 55 | AISGSGGSTY SEQ ID NO: 56 | DLDYRFSGFDV SEQ ID NO: 57 | QASQDISNYLN SEQ ID NO: 58 | DASNLET SEQ ID NO: 59 | QQFAAIPLT SEQ ID NO: 60 |

For example, using the CDRs and $V_H$ and $V_L$ domain information above, IgG$_1$ antibodies can be prepared having the following exemplary heavy chains (HC) and light chain (LC) sequences with amino acid sequences of SEQ ID Nos:13-24. Most typically, but not necessarily, HC and LC with the same preceding numeral (e.g., 64-6) will be present in a TIM3 binding antibody. However, other TIM3 binding antibodies may have a heavy chain and a light chain with non-identical preceding numeral.

```
64-6 HC amino acid sequence:
                                                (SEQ ID NO: 13)
EVQLVESGGGLVQPGGSLRLSCAASGFTFSRYAMHWVRQAPGKGLEWVSAI

SGSGGYTYYADSVKGRFTISRDNSKNTLYLQMNSLRAEDTAVYYCARDRHWVLSA

FDVWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQP

ENNYKTTPPVLDSDGSFFLYSKLTVDKSRWQQGNVFScSVMHEALHNHYTQKSLSL

SPGK 64-6 LC amino acid sequence:
                                                (SEQ ID NO: 14)
DIQMTQSPSSLSASVGDRVTITCQASQDISNYLNWYQQKPGKAPKLLIYDASN

LETGVPSRFSGSGSGTDFTFTISSLQPEDIATYYCQQYDTFPFTFGQGTKVEIKRTVAA

PSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC 64-15 HC amino acid sequence:
                                                (SEQ ID NO: 15)
EVQLVESGGGLVQPGGSLRLSCAASGFTFSSYYMHWVRQAPGKGLEWVSGI

SGSGGSTYYADSVKGRFTISRDNSKNTLYLQMNSLRAEDTAVYYCARGRGAWPFTR

VVAFDVWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFScSVMHEALHNHYTQKS

LSLSPGK 64-15 LC amino acid sequence:
                                                (SEQ ID NO: 16)
DIQMTQSPSSLSASVGDRVTITCQASQDISNYLNWYQQKPGKAPKLLIYDASN

LETGVPSRFSGSGSGTDFTFTISSLQPEDIATYYCQQWTALPLTFGQGTKVEIKRTVAA

PSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC 64-31 HC amino acid sequence:
                                                (SEQ ID NO: 17)
MEVQLVESGGGLVQPGGSLRLSCAASGFTFSAYAMHWVRQAPGKGLEWVS

AINGNGGRTYYADSVKGRFTISRDNSKNTLYLQMNSLRAEDTAVYYCARDLTRTVP

FAFDVWGQGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKA
```

```
LPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFScSVMHEALHNHYTQKSL

SLSPGK 64-31 LC amino acid sequence:
                                                (SEQ ID NO: 18)
DIQMTQSPSSLSASVGDRVTITCQASQDISNYLNWYQQKPGKAPKLLIYDASN

LETGVPSRFSGSGSGTDFTFTISSLQPEDIATYYCQQATGWPFTFGQGTKVEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC 64-32 HC amino acid sequence:
                                                (SEQ ID NO: 19)
MEVQLVESGGGLVQPGGSLRLSCAASGFTFSKYAMHWVRQAPGKGLEWVS

AISGSGGYTYYADSVKGRFTISRDNSKNTLYLQMNSLRAEDTAVYYCARDLDFRIVG

FDVWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHYTQKSLSL

SPGK 64-32 LC amino acid sequence:
                                                (SEQ ID NO: 20)
DIQMTQSPSSLSASVGDRVTITCQASQDISNYLNWYQQKPGKAPKLLIYDASN

LETGVPSRFSGSGSGTDFTFTISSLQPEDIATYYCQQFNTVPLTFGQGTKVEIKRTVAA

PSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC 64-39 HC amino acid sequence:
                                                (SEQ ID NO: 21)
MEVQLVESGGGLVQPGGSLRLSCAASGFTFSRYAMHWVRQAPGKGLEWVS

GISGSGGGTYYADSVKGRFTISRDNSKNTLYLQMNSLRAEDTAVYYCARDLDYRVS

GFDVWGQGTLVTVSSASTKGPSVFPLAPSSKSTSGGTAALGCLVKDYFPEPVTVSWN

SGALTSGVHTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHYTQKSLSL

SPGK 64-39 LC amino acid sequence:
                                                (SEQ ID NO: 22)
DIQMTQSPSSLSASVGDRVTITCQASQDISNYLNWYQQKPGKAPKLLIYDASN

LETGVPSRFSGSGSGTDFTFTISSLQPEDIATYYCQQFYSVPLTFGQGTKVEIKRTVAA

PSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC 66-6 HC amino acid sequence:
                                                (SEQ ID NO: 23)
MEVQLVESGGGLVQPGGSLRLSCAASGFTFSKYAMHWVRQAPGKGLEWVS

AISGSGGSTYYADSVKGRFTISRDNSKNTLYLQMNSLRAEDTAVYYCARDLDYRFSG
```

```
FDVWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHYTQKSLSL

SPGK 66-6 LC amino acid sequence:
                                                      (SEQ ID NO: 24)
DIQMTQSPSSLSASVGDRVTITCQASQDISNYLNWYQQKPGKAPKLLIYDASN

LETGVPSRFSGSGSGTDFTFTISSLQPEDIATYYCQQFAAIPLTFGQGTKVEIKRTVAAP

SVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC
```

In one typical example, the inventors prepared antibodies using the above HC and LC sequences with matching preceding numbers and tested the so prepared antibodies for TIM3 binding. Table 2 depicts exemplary results for determination of dissociation constants of the antibodies. More specifically, $K_D$ determination was done by SPR (Pioneer FE) or Octet (Red96e) at 25° C. or 37° C. All values are ×10$^{-9}$M. anti-TIM-3 IgG1 antibodies were captured on the chip surface using anti-human Fc antibody (SPR) or AHC sensor (Octet), and human TIM-3 was the analyte.

TABLE 2

| aTIM-3 IgG1 | 25° C. | 37° C. |
|---|---|---|
| 64-6 | 0.46 | 2.50 |
| 64-15 | 0.71 | 5.40 |
| 64-31 | 10.4 | 36.5 |
| 64-32 | 0.39 | 0.92 |
| 64-39 | 1.53 | 6.39 |
| 66-6 | 1.69 | 7.01 |

Notably, despite being the same type of antibody (here: IgG$_1$) with otherwise identical framework regions, the tested antibodies exhibited unexpected affinity differences spanning almost three orders of magnitude as can be seen from Table 2 above. Here, antibodies 64-6, 64-15, and 64-32 had sub-nanomolar $K_D$ values at 25° C., while antibodies 64-39 and 66-6 had single-digit $K_D$ values at 25° C., and antibody 64-31 had a double-digit $K_D$ value at 25° C. Similarly, the $K_D$ differences between 25° C. and 37° C. for each antibody were unexpectedly low for antibodies 64-32 and 64-31 (2.36× and 3.51×) whereas antibodies 64-6, 64-39, and 66-6 were higher (5.43×, 4.18×, 4.15×), and antibody 64-15 was even higher (7.61×). Viewed from a different perspective, antibodies 64-6 and 64-32 had an affinity to TIM-3 at physiological temperatures that was two orders of magnitude stronger than antibody 64-31.

Of course, it should be appreciated that the inventive subject matter is not limited to the exact sequences noted above, but one or more of the sequences may include one or more amino acid changes. Most preferably, the changes will not result in a substantial reduction of specificity and/or affinity. Thus, contemplated amino acid changes will typically be in the framework regions of the $V_H$ and/or $V_L$ domains, and/or in the constant regions of HC and/or LC.

Viewed from a different perspective, amino acid changes will preferably not be present in the CDR region. For example, contemplated sequences will have between 98-99% identity or homology, or between 96-98% identity or homology, or between 92-96% identity or homology, or between 85-92% identity or homology, or between 75-85% identity or homology, most typically (but not necessarily) with the changed amino acids outside the CDRs. Among other options for amino acid changes, one or more amino acids can be changed to 'humanize' a non-human antibody, and/or to move or eliminate one or more glycosylation sites.

Moreover, it should be noted that contemplated antibodies will expressly include various forms such as monoclonal antibodies, multi-specific antibodies, human antibodies, humanized antibodies, synthetic antibodies, chimeric antibodies, single domain antibodies, single-chain Fvs (scFv), single chain antibodies, disulfide-linked Fvs (sdFv), BiKes, and TriKes as is described in more detail below. Of course, it should also be noted that the term antibody expressly includes all classes of immunoglobulin molecules (e.g., IgG, IgE, IgM, IgD, IgA, and IgY), as well as the corresponding subclasses (e.g., IgG$_1$, IgG$_2$, IgG$_3$, IgG$_4$, IgA$_1$, IgA$_2$).

With respect to contemplated antibody fragments it should be noted that fragments will include one or more portions of an antibody that contains CDRs (typically all CDRs of at least one of $V_H$ and $V_L$), and optionally the framework residues. Thus, antibody fragments will in most cases exhibit an ability to specifically bind to the antigen (here: an epitope of TIM3). Among other fragments, especially contemplated fragments include Fab', F(ab')$_2$, Fv, scFv, and mutants thereof, naturally occurring variants, as well as fusion proteins with various non-antibody polypeptides (e.g., toxin, antigen recognition site for a different antigen, enzyme, receptor, receptor ligand, etc.). Viewed from a different perspective, contemplated antibody fragments will have an amino acid sequence of at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

In further contemplated aspects, the antibody of fragment thereof may be used for in vitro or in vivo diagnosis and as such be coupled to a detectable label. For example, suitable detectable labels include various enzymes, fluorescent materials, luminescent materials, bioluminescent materials, radioactive materials, positron emitting metals, and nonradioactive paramagnetic metal ions. The detectable label can be coupled or conjugated either directly to the antibody or indirectly, through an intermediate (e.g., chemical or biological linker) using techniques known in the art. Additionally, or alternatively, contemplated antibodies and fragments thereof may also be coupled to a solid support, which is particularly useful for immunoassays or purification of TIM3 or cells expressing TIM3. For example, suitable supports include magnetic beads, glass, cellulose, polyacrylamide, nylon, polystyrene, polyvinyl chloride, and polypropylene.

Contemplated antibodies and fragments thereof may also be coupled to or comprise a therapeutic agent to target the agent to a cell expressing TIM3. For example, especially contemplated therapeutic agents include chemotherapeutic drugs, radionuclide, and immune stimulants (e.g., cytokine, a cytokine analog, a chemokine, or a checkpoint inhibitor). There are numerous manners of preparing antibody-drug conjugates, and all of these are deemed suitable for use herein.

In especially preferred aspects, contemplated antibodies or fragments thereof may also be prepared as chimeric proteins in which at least one portion of the antibody is continuous with a second polypeptide (optionally via a preferably flexible linker). For example, suitable chimeric proteins may be configured as chimeric antigen receptors (CAR) that may have an intracellular signaling portion, a transmembrane portion, and an extracellular recognition domain. In such case, it is generally contemplated that the recognition domain includes an antibody fragment (e.g., scFv or single domain) and/or that the intracellular signaling domain comprises an activating/ITAM motif. Among other options, contemplated may be first, second, or third generation CARs with a variety of domains known in the art. For example, suitable CARS will include a CD8 hinge portion, a CD28 transmembrane domain, and a CD3zeta (CD3ζ) or Fc receptor epsilon (FcεRIγ) signaling domain. Alternatively, the signaling domain may also include one or more of a CD28 signaling domain, a 4-1BB signaling domain, and a CD3zeta (CD3ζ) signaling domain. Among other options, such chimeric antigen receptors are preferably expressed in cytotoxic immune competent cells, and especially in NK cells and/or T cells.

On the other hand, and especially where the anti-TIM3 antibody or fragment thereof is used to additionally mediate cell or receptor/ligand contact, contemplated chimeric proteins may be constructed as a bispecific fusion protein, as a bispecific killer cell engager (BiKE), or as a trispecific killer cell engager (TriKe). For example, a bispecific fusion protein may comprise the anti-TIM3 antibody or portion thereof and a second affinity ligand that selectively binds to a desired target. Such target may be a soluble protein or a cell-bound protein, and especially contemplated targets include PD-L1. On the other hand, contemplated chimeric molecules may be constructed as bispecific polypeptides (e.g., first scFv coupled via linker to second scFv) in which one portion comprises the anti-TIM3 antibody or portion thereof and in which the other portion has a binder to a marker specific for an immune competent cell (e.g., anti-CD3).

In further contemplated aspects, the anti-TIM3 antibody or portion thereof may also be coupled to an IgG-Fc/IL15Rα/IL15 hybrid (e.g., ALT803). For example, the anti-TIM3 antibody fragment could be a scFv portion that is coupled to one or both arms of the hybrid to so form a TxM (see TxM technology at URL:Altorbioscience.com). Or the anti-TIM3 antibody fragment could be a scFv portion that is coupled to one arm of the hybrid, while the other arm of the hybrid could be a scFv portion that binds PD-L1 (or other immune related ligand).

As should be appreciated, nucleic acids encoding contemplated anti-TIM3 antibodies are also expressly considered herein, and the skilled artisan will be readily able to prepare such nucleic acids (e.g., DNA, RNA) and recombinant entities comprising such nucleic acids. Among other options, suitable recombinant entities include yeast, bacterial, and viral expression vectors, linear DNA for genome editing or other integration, RNA, etc. of course, it should be recognized that the recombinant nucleic acids will include suitable regulatory elements to allow for expression of the recombinant construct. Moreover, it should be noted that the nucleic acid will typically make use of codon-optimization with respect to the host cells that include and express the recombinant nucleic acid.

As will be readily appreciated, use of anti-TIM3 antibodies, fragments thereof, or chimeric proteins containing anti-TIM3 antibodies or fragments thereof is particularly advantageous where immune suppression mediated by TIM3 is to be reduced or inhibited. Consequently, antibodies or portions thereof can be especially useful in the reversal or reduction of immune suppression via TIM3 signaling. Moreover, where cancer cell express and display TIM3, the cells may offer a further therapeutic target (e.g., via targeting with a chimeric molecule that has a TIM3 binding portion and an immune stimulatory portion (e.g., ALT-803)).

In view of these findings, the inventors also contemplate use of various recombinant TIM3 binding molecules such as antibodies and fragments thereof as well as cells expressing anti-TIM3 CAR molecules and pharmaceutical compositions comprising same. Most typically, such recombinant proteins may be soluble forms of antibodies and fragments thereof, soluble chimeric molecules comprising a TIM3 binding portion, or membrane bound molecules such as CAR comprising a TIM3 binding portion. For example, recombinant TIM3 binding CARs may be expressed in a cytotoxic cell such as a T cell, a natural killer cell, or an NKT cell.

It is contemplated that such prepared or generated pharmaceutical composition can be administered to a patient having a tumor to increase effectiveness of immune therapy to so treat the tumor (e.g., to modulate (e.g., reduce, abrogate, etc.) immune suppression by the tumor, to reduce the tumor size, etc.). In some embodiments, pharmaceutical composition and/or the tumor vaccine can be administered via systemic injection including subcutaneous, subdermal injection, or intravenous injection. In other embodiments, where the systemic injection may not be efficient (e.g., for brain tumors, etc.) or more localized treatment is desired, it is contemplated that the recombinant immunoglobulin protein complex and/or pharmaceutical compositions can be administered via intratumoral injection. As used herein, the term "administering" refers to both direct and indirect administration of the compounds and compositions contemplated herein, where direct administration is typically performed by a health care professional (e.g., physician, nurse, etc.), while indirect administration typically includes a step of providing or making the compounds and compositions available to the health care professional for direct administration.

With respect to dose and schedule of the administration, it is contemplated that the dose and/or schedule may vary depending on depending on the type of protein, protein complex, or the type of the pharmaceutical composition (e.g., virus, bacteria, yeast, in combination with recombinant protein complex, etc.), type and prognosis of disease (e.g., tumor type, size, location), health status of the patient (e.g., including age, gender, etc.). While it may vary, the dose and schedule may be selected and regulated such that the formulation does not provide any significant toxic effect to the host normal cells, yet sufficient to be reduce immune suppression by reduced T cell differentiation and/or activation in the tumor microenvironment. Thus, in a preferred embodiment, an optimal or desired condition of administering the formulation can be determined based on a predetermined threshold. For example, the predetermined threshold may be a predetermined local or systemic concentration of T-cell activating, or T-cell released cytokines (e.g., IL-2, IL-12, IFN-γ, IL-12, IL-23, IL-1b, IL-6, or TGF-β, etc.) in the tumor microenvironment. Therefore, administration conditions are typically adjusted to have one or more of those cytokines increased in the tumor microenvironment at least 20%, at least 30%, at least 50%, at least 60%, at least 70% at least for 24 hours, 48 hours, 72 hours, 7 days, etc. Moreover, it is contemplated that the compounds and compositions presented herein may be co-administered (contemporaneously or sequentially) with NK cells. For example, suitable NK cells include autologous NK cells as well as NK92 cells and derivatives thereof (e.g., aNK cells, haNK cells, taNK cells, al commercially available from NantKwest, 9920 Jefferson Blvd. Culver City, Calif. 90232).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An isolated antibody or fragment thereof, wherein the antibody or fragment thereof binds to T-cell immunoglobulin mucin receptor 3 (TIM3), comprising:
   a variable heavy chain (VH) domain and a variable light chain (VL) domain;
   wherein the VH domain is selected form the group consisting of SEQ ID NO:1, SEQ ID NO:3, SEQ ID NO:5, SEQ ID NO:7, SEQ ID NO:9, and SEQ ID NO:11; and
   wherein the VL domain is selected form the group consisting of SEQ ID NO:2, SEQ ID NO:4, SEQ ID NO:6, SEQ ID NO:8, SEQ ID NO:10, and SEQ ID NO:12.

2. The antibody or fragment of claim 1, comprising $VH_{64-6}$ (SEQ ID NO:1) and $VL_{64-6}$ (SEQ ID NO:2), optionally coupled together by a linker to form an scFv.

3. The antibody or fragment of claim 1, comprising $VH_{64-15}$ (SEQ ID NO:3) and $VL_{64-15}$ (SEQ ID NO:4), optionally coupled together by a linker to form an scFv.

4. The antibody or fragment of claim 1, comprising $VH_{64-31}$ (SEQ ID NO:5) and $VL_{64-31}$ (SEQ ID NO:6), optionally coupled together by a linker to form an scFv.

5. The antibody or fragment of claim 1, comprising $VH_{64-32}$ (SEQ ID NO:7) and $VL_{64-32}$ (SEQ ID NO:8), optionally coupled together by a linker to form an scFv.

6. The antibody or fragment of claim 1, comprising $VH_{64-39}$ (SEQ ID NO:9) and $VL_{64-39}$ (SEQ ID NO:10), optionally coupled together by a linker to form an scFv.

7. The antibody or fragment of claim 1, comprising $VH_{66}$-6 (SEQ ID NO:11) and $VL_{66}$-6 (SEQ ID NO:12), optionally coupled together by a linker to form an scFv.

8. The antibody or fragment of claim 1, further comprising a therapeutic agent or a detectable label coupled to the antibody or fragment.

9. The antibody or fragment of claim 1, wherein the therapeutic agent is a chemotherapeutic drug, a radionuclide, or an immune stimulant selected from the group consisting of a cytokine, a cytokine analog, a chemokine, or a checkpoint inhibitor.

10. A chimeric protein comprising the antibody or fragment of claim 1.

11. The chimeric protein of claim 10 wherein the chimeric protein is a chimeric antigen receptor (CAR) or a bispecific fusion protein.

12. The chimeric protein of claim 11 wherein the CAR has a CD3zeta (CD3ζ) or Fc receptor epsilon (FcεRIγ) signaling domain.

13. The chimeric protein of claim 11 wherein the CAR has at least one of a CD28 signaling domain, a 4-1BB signaling domain, and a CD3zeta (CD3ζ) signaling domain.

14. The chimeric protein of claim 11 wherein the CAR has a CD8 hinge domain and a CD28 transmembrane domain.

15. The chimeric protein of claim 11 wherein the CAR is a recombinant CAR expressed in and coupled to a surface of an NK cell or a cytotoxic T cell.

16. The chimeric protein of claim 11 wherein the bispecific fusion protein comprises a IgG Fc portion, and optionally further comprises at least one of an IL15α receptor portion, an IL15 portion, and an IL15 superagonist portion.

17. The chimeric protein of claim 11 configured as a bispecific killer cell engager (BiKE) or a trispecific killer cell engager (TriKe).

18. A recombinant nucleic acid encoding the isolated antibody or fragment of claim 1 or the chimeric protein of claim 10.

19. The recombinant nucleic acid of claim 18, wherein the nucleic acid is in an expression vector or in a recombinant viral genome, or is in form of a linear DNA.

20. The recombinant nucleic acid of claim 18, wherein the nucleic acid is an RNA.

* * * * *

SEQUENCE LISTING

```
<160> NUMBER OF SEQ ID NOS: 60

<210> SEQ ID NO 1
<211> LENGTH: 120
<212> TYPE: PRT
<213> ORGANISM: Artificial Sequence
<220> FEATURE:
<223> OTHER INFORMATION: 64-6 VH amino acid sequence

<400> SEQUENCE: 1
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg His Trp Val Leu Ser Ala Phe Asp Val Trp Gly Gln
                100                 105                 110

Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: 64-6 VL amino acid sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Thr Phe Pro Phe
                85                  90                  95

Thr Phe Gly Gln Gly Thr Lys Val Glu Ile Lys
                100                 105

<210> SEQ ID NO 3
<211> LENGTH: 124
<212> TYPE: PRT
<213> ORGANISM: Artificial Sequence
<220> FEATURE:
<223> OTHER INFORMATION: 64-15 VH amino acid sequence

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                        85                  90                  95

Ala Arg Gly Arg Gly Ala Trp Pro Phe Thr Arg Val Val Ala Phe Asp
                100                 105                 110

Val Trp Gly Gln Gly Thr Leu Val Thr Val Ser Ser
        115                 120
```

<210> SEQ ID NO 4
<211> LENGTH: 107
<212> TYPE: PRT
<213> ORGANISM: Artificial Sequence
<220> FEATURE:
<223> OTHER INFORMATION: 64-15 VL amino acid sequence

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Trp Thr Ala Leu Pro Leu
                85                  90                  95

Thr Phe Gly Gln Gly Thr Lys Val Glu Ile Lys
            100                 105
```

<210> SEQ ID NO 5
<211> LENGTH: 122
<212> TYPE: PRT
<213> ORGANISM: Artificial Sequence
<220> FEATURE:
<223> OTHER INFORMATION: 64-31 VH amino acid sequence

<400> SEQUENCE: 5

```
Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ala
                20                  25                  30

Tyr Ala Met His Trp Val Arg Gln Ala Pro Gly Lys Gly Leu Glu Trp
            35                  40                  45

Val Ser Ala Ile Asn Gly Asn Gly Gly Arg Thr Tyr Tyr Ala Asp Ser
        50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Leu Thr Arg Thr Val Pro Phe Ala Phe Asp Val Trp
                100                 105                 110

Gly Gln Gly Thr Leu Val Thr Val Ser Ser
            115                 120
```

<210> SEQ ID NO 6
<211> LENGTH: 107

```
<212> TYPE: PRT
<213> ORGANISM: Artificial Sequence
<220> FEATURE:
<223> OTHER INFORMATION: 64-31 VL amino acid sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Thr Gly Trp Pro Phe
                85                  90                  95

Thr Phe Gly Gln Gly Thr Lys Val Glu Ile Lys
            100                 105

<210> SEQ ID NO 7
<211> LENGTH: 121
<212> TYPE: PRT
<213> ORGANISM: Artificial Sequence
<220> FEATURE:
<223> OTHER INFORMATION: 64-32 VH amino acid sequence

<400> SEQUENCE: 7

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Lys
            20                  25                  30

Tyr Ala Met His Trp Val Arg Gln Ala Pro Gly Lys Gly Leu Glu Trp
        35                  40                  45

Val Ser Ala Ile Ser Gly Ser Gly Gly Tyr Thr Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Leu Asp Phe Arg Ile Val Gly Phe Asp Val Trp Gly
            100                 105                 110

Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: 64-32 VL amino acid sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
```

```
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Thr Val Pro Leu
                85                  90                  95

Thr Phe Gly Gln Gly Thr Lys Val Glu Ile Lys
            100                 105
```

<210> SEQ ID NO 9
<211> LENGTH: 121
<212> TYPE: PRT
<213> ORGANISM: Artificial Sequence
<220> FEATURE:
<223> OTHER INFORMATION: 64-39 VH amino acid sequence

<400> SEQUENCE: 9

```
Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Arg
            20                  25                  30

Tyr Ala Met His Trp Val Arg Gln Ala Pro Gly Lys Gly Leu Glu Trp
        35                  40                  45

Val Ser Gly Ile Ser Gly Ser Gly Gly Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Leu Asp Tyr Arg Val Ser Gly Phe Asp Val Trp Gly
            100                 105                 110

Gln Gly Thr Leu Val Thr Val Ser Ser
        115                 120
```

<210> SEQ ID NO 10
<211> LENGTH: 107
<212> TYPE: PRT
<213> ORGANISM: Artificial Sequence
<220> FEATURE:
<223> OTHER INFORMATION: 64-39 VL amino acid sequence

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Tyr Ser Val Pro Leu
                85                  90                  95

Thr Phe Gly Gln Gly Thr Lys Val Glu Ile Lys
            100                 105
```

```
<210> SEQ ID NO 11
<211> LENGTH: 121
<212> TYPE: PRT
<213> ORGANISM: Artificial Sequence
<220> FEATURE:
<223> OTHER INFORMATION: 66-6 VH amino acid sequence

<400> SEQUENCE: 11

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Lys
            20                  25                  30

Tyr Ala Met His Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Leu Asp Tyr Arg Phe Ser Gly Phe Asp Val Trp Gly
            100                 105                 110

Gln Gly Thr Leu Val Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: 66-6 VL amino acid sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Ala Ala Ile Pro Leu
                85                  90                  95

Thr Phe Gly Gln Gly Thr Lys Val Glu Ile Lys
            100                 105

<210> SEQ ID NO 13
<211> LENGTH: 450
<212> TYPE: PRT
<213> ORGANISM: Artificial Sequence
<220> FEATURE:
<223> OTHER INFORMATION: 64-6 HC amino acid sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
```

```
            20                  25                  30
Ala Met His Trp Val Arg Gln Ala Pro Gly Lys Gly Leu Glu Trp Val
            35                  40                  45

Ser Ala Ile Ser Gly Ser Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg His Trp Val Leu Ser Ala Phe Asp Val Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445
```

```
Gly Lys
    450

<210> SEQ ID NO 14
<211> LENGTH: 214
<212> TYPE: PRT
<213> ORGANISM: Artificial Sequence
<220> FEATURE:
<223> OTHER INFORMATION: 64-6 LC amino acid sequence

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Thr Phe Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 454
<212> TYPE: PRT
<213> ORGANISM: Artificial Sequence
<220> FEATURE:
<223> OTHER INFORMATION: 64-15 HC amino acid sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
```

```
              65                  70                  75                  80
         Leu Gln Met Asn Ser Leu Arg Ala Glu Asp Thr Ala Val Tyr Tyr Cys
                             85                  90                  95

Ala Arg Gly Arg Gly Ala Trp Pro Phe Thr Arg Val Val Ala Phe Asp
                        100                 105                 110

Val Trp Gly Gln Gly Thr Leu Val Thr Val Ser Ser Ala Ser Thr Lys
                    115                 120                 125

Gly Pro Ser Val Phe Pro Leu Ala Pro Ser Ser Lys Ser Thr Ser Gly
                130                 135                 140

Gly Thr Ala Ala Leu Gly Cys Leu Val Lys Asp Tyr Phe Pro Glu Pro
         145                 150                 155                 160

Val Thr Val Ser Trp Asn Ser Gly Ala Leu Thr Ser Gly Val His Thr
                             165                 170                 175

Phe Pro Ala Val Leu Gln Ser Ser Gly Leu Tyr Ser Leu Ser Ser Val
                        180                 185                 190

Val Thr Val Pro Ser Ser Ser Leu Gly Thr Gln Thr Tyr Ile Cys Asn
                    195                 200                 205

Val Asn His Lys Pro Ser Asn Thr Lys Val Asp Lys Lys Val Glu Pro
                210                 215                 220

Lys Ser Cys Asp Lys Thr His Thr Cys Pro Pro Cys Pro Ala Pro Glu
         225                 230                 235                 240

Leu Leu Gly Gly Pro Ser Val Phe Leu Phe Pro Pro Lys Pro Lys Asp
                             245                 250                 255

Thr Leu Met Ile Ser Arg Thr Pro Glu Val Thr Cys Val Val Val Asp
                        260                 265                 270

Val Ser His Glu Asp Pro Glu Val Lys Phe Asn Trp Tyr Val Asp Gly
                    275                 280                 285

Val Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp Trp
         305                 310                 315                 320

Leu Asn Gly Lys Glu Tyr Lys Cys Lys Val Ser Asn Lys Ala Leu Pro
                             325                 330                 335

Ala Pro Ile Glu Lys Thr Ile Ser Lys Ala Lys Gly Gln Pro Arg Glu
                        340                 345                 350

Pro Gln Val Tyr Thr Leu Pro Pro Ser Arg Asp Glu Leu Thr Lys Asn
                    355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
         385                 390                 395                 400

Thr Pro Pro Val Leu Asp Ser Asp Gly Ser Phe Phe Leu Tyr Ser Lys
                             405                 410                 415

Leu Thr Val Asp Lys Ser Arg Trp Gln Gln Gly Asn Val Phe Ser Cys
                        420                 425                 430

Ser Val Met His Glu Ala Leu His Asn His Tyr Thr Gln Lys Ser Leu
                    435                 440                 445

Ser Leu Ser Pro Gly Lys
                450

<210> SEQ ID NO 16
<211> LENGTH: 214
<212> TYPE: PRT
<213> ORGANISM: Artificial Sequence
```

<220> FEATURE:
<223> OTHER INFORMATION: 64-15 LC amino acid sequence

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Trp Thr Ala Leu Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 17
<211> LENGTH: 452
<212> TYPE: PRT
<213> ORGANISM: Artificial Sequence
<220> FEATURE:
<223> OTHER INFORMATION: 64-31 HC amino acid sequence

<400> SEQUENCE: 17

```
Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ala
            20                  25                  30

Tyr Ala Met His Trp Val Arg Gln Ala Pro Gly Lys Gly Leu Glu Trp
        35                  40                  45

Val Ser Ala Ile Asn Gly Asn Gly Gly Arg Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Leu Thr Arg Thr Val Pro Phe Ala Phe Asp Val Trp
            100                 105                 110

Gly Gln Gly Thr Leu Val Thr Val Ser Ser Ala Ser Thr Lys Gly Pro
```

```
            115                 120                 125
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 18
<211> LENGTH: 214
<212> TYPE: PRT
<213> ORGANISM: Artificial Sequence
<220> FEATURE:
<223> OTHER INFORMATION: 64-31 LC amino acid sequence

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
```

```
                20                  25                  30
Leu Asn Trp Tyr Gln Gln Lys Pro Gly Lys Ala Pro Lys Leu Leu Ile
                35                  40                  45

Tyr Asp Ala Ser Asn Leu Glu Thr Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Thr Gly Trp Pro Phe
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 19
<211> LENGTH: 451
<212> TYPE: PRT
<213> ORGANISM: Artificial Sequence
<220> FEATURE:
<223> OTHER INFORMATION: 64-32 HC amino acid sequence

<400> SEQUENCE: 19

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Lys
                20                  25                  30

Tyr Ala Met His Trp Val Arg Gln Ala Pro Gly Lys Gly Leu Glu Trp
            35                  40                  45

Val Ser Ala Ile Ser Gly Ser Gly Gly Tyr Thr Tyr Tyr Ala Asp Ser
        50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Leu Asp Phe Arg Ile Val Gly Phe Asp Val Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
                    165                 170                 175
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 20
<211> LENGTH: 214
<212> TYPE: PRT
<213> ORGANISM: Artificial Sequence
<220> FEATURE:
<223> OTHER INFORMATION: 64-32 LC amino acid sequence

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
```

```
                65                  70                  75                  80
Glu Asp Ile Ala Thr Tyr Tyr Cys Gln Gln Phe Asn Thr Val Pro Leu
                        85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 21
<211> LENGTH: 451
<212> TYPE: PRT
<213> ORGANISM: Artificial Sequence
<220> FEATURE:
<223> OTHER INFORMATION: 64-39 HC amino acid sequence

<400> SEQUENCE: 21

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Arg
            20                  25                  30

Tyr Ala Met His Trp Val Arg Gln Ala Pro Gly Lys Gly Leu Glu Trp
        35                  40                  45

Val Ser Gly Ile Ser Gly Ser Gly Gly Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Leu Asp Tyr Arg Val Ser Gly Phe Asp Val Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
```

```
                210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 22
<211> LENGTH: 214
<212> TYPE: PRT
<213> ORGANISM: Artificial Sequence
<220> FEATURE:
<223> OTHER INFORMATION: 64-39 LC amino acid sequence

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Tyr Ser Val Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
                195                 200                 205
Phe Asn Arg Gly Glu Cys
    210

<210> SEQ ID NO 23
<211> LENGTH: 451
<212> TYPE: PRT
<213> ORGANISM: Artificial Sequence
<220> FEATURE:
<223> OTHER INFORMATION: 66-6 HC amino acid sequence

<400> SEQUENCE: 23

Met Glu Val Gln Leu Val Glu Ser Gly Gly Gly Leu Val Gln Pro Gly
1               5                   10                  15
Gly Ser Leu Arg Leu Ser Cys Ala Ala Ser Gly Phe Thr Phe Ser Lys
            20                  25                  30
Tyr Ala Met His Trp Val Arg Gln Ala Pro Gly Lys Gly Leu Glu Trp
        35                  40                  45
Val Ser Ala Ile Ser Gly Ser Gly Gly Ser Thr Tyr Tyr Ala Asp Ser
    50                  55                  60
Val Lys Gly Arg Phe Thr Ile Ser Arg Asp Asn Ser Lys Asn Thr Leu
65                  70                  75                  80
Tyr Leu Gln Met Asn Ser Leu Arg Ala Glu Asp Thr Ala Val Tyr Tyr
                85                  90                  95
Cys Ala Arg Asp Leu Asp Tyr Arg Phe Ser Gly Phe Asp Val Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
```

```
                260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 24
<211> LENGTH: 214
<212> TYPE: PRT
<213> ORGANISM: Artificial Sequence
<220> FEATURE:
<223> OTHER INFORMATION: 66-6 LC amino acid sequence

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Ala Ala Ile Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 6
<212> TYPE: PRT
<213> ORGANISM: Artificial Sequence
<220> FEATURE:
<223> OTHER INFORMATION: 64-6 CDR-H1

<400> SEQUENCE: 25

Ser Arg Tyr Ala Met His
1               5

<210> SEQ ID NO 26
<211> LENGTH: 10
<212> TYPE: PRT
<213> ORGANISM: Artificial Sequence
<220> FEATURE:
<223> OTHER INFORMATION: 64-6 CDR-H2

<400> SEQUENCE: 26

Ala Ile Ser Gly Ser Gly Gly Tyr Thr Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: 64-6 CDR-H3

<400> SEQUENCE: 27

Asp Arg His Trp Val Leu Ser Ala Phe Asp Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: 64-6 CDR-L1

<400> SEQUENCE: 28

Gln Ala Ser Gln Asp Ile Ser Asn Tyr Leu Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: 64-6 CDR-L2

<400> SEQUENCE: 29

Asp Ala Ser Asn Leu Glu Thr
1               5

<210> SEQ ID NO 30
<211> LENGTH: 9
```

```
<212> TYPE: PRT
<213> ORGANISM: Artificial Sequence
<220> FEATURE:
<223> OTHER INFORMATION: 64-6 CDR-L3

<400> SEQUENCE: 30

Gln Gln Tyr Asp Thr Phe Pro Phe Thr
1               5

<210> SEQ ID NO 31
<211> LENGTH: 6
<212> TYPE: PRT
<213> ORGANISM: Artificial Sequence
<220> FEATURE:
<223> OTHER INFORMATION: 64-15 CDR-H1

<400> SEQUENCE: 31

Ser Ser Tyr Tyr Met His
1               5

<210> SEQ ID NO 32
<211> LENGTH: 10
<212> TYPE: PRT
<213> ORGANISM: Artificial Sequence
<220> FEATURE:
<223> OTHER INFORMATION: 64-15 CDR-H2

<400> SEQUENCE: 32

Gly Ile Ser Gly Ser Gly Gly Ser Thr Tyr
1               5                   10

<210> SEQ ID NO 33
<211> LENGTH: 18
<212> TYPE: PRT
<213> ORGANISM: Artificial Sequence
<220> FEATURE:
<223> OTHER INFORMATION: 64-15 CDR-H3

<400> SEQUENCE: 33

Cys Ala Arg Gly Arg Gly Ala Trp Pro Phe Thr Arg Val Val Ala Phe
1               5                   10                  15

Asp Val

<210> SEQ ID NO 34
<211> LENGTH: 11
<212> TYPE: PRT
<213> ORGANISM: Artificial Sequence
<220> FEATURE:
<223> OTHER INFORMATION: 64-15 CDR-L1

<400> SEQUENCE: 34

Gln Ala Ser Gln Asp Ile Ser Asn Tyr Leu Asn
1               5                   10

<210> SEQ ID NO 35
<211> LENGTH: 7
<212> TYPE: PRT
<213> ORGANISM: Artificial Sequence
<220> FEATURE:
<223> OTHER INFORMATION: 64-15 CDR-L2

<400> SEQUENCE: 35

Asp Ala Ser Asn Leu Glu Thr
1               5

<210> SEQ ID NO 36
```

```
<211> LENGTH: 9
<212> TYPE: PRT
<213> ORGANISM: Artificial Sequence
<220> FEATURE:
<223> OTHER INFORMATION: 64-15 CDR-L3

<400> SEQUENCE: 36

Gln Gln Trp Thr Ala Leu Pro Leu Thr
1               5

<210> SEQ ID NO 37
<211> LENGTH: 6
<212> TYPE: PRT
<213> ORGANISM: Artificial Sequence
<220> FEATURE:
<223> OTHER INFORMATION: 64-31 CDR-H1

<400> SEQUENCE: 37

Ser Ala Tyr Ala Met His
1               5

<210> SEQ ID NO 38
<211> LENGTH: 10
<212> TYPE: PRT
<213> ORGANISM: Artificial Sequence
<220> FEATURE:
<223> OTHER INFORMATION: 64-31 CDR-H2

<400> SEQUENCE: 38

Ala Ile Asn Gly Asn Gly Gly Arg Thr Tyr
1               5                   10

<210> SEQ ID NO 39
<211> LENGTH: 12
<212> TYPE: PRT
<213> ORGANISM: Artificial Sequence
<220> FEATURE:
<223> OTHER INFORMATION: 64-31 CDR-H3

<400> SEQUENCE: 39

Asp Leu Thr Arg Thr Val Pro Phe Ala Phe Asp Val
1               5                   10

<210> SEQ ID NO 40
<211> LENGTH: 11
<212> TYPE: PRT
<213> ORGANISM: Artificial Sequence
<220> FEATURE:
<223> OTHER INFORMATION: 64-31 CDR-L1

<400> SEQUENCE: 40

Gln Ala Ser Gln Asp Ile Ser Asn Tyr Leu Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: 64-31 CDR-L2

<400> SEQUENCE: 41

Asp Ala Ser Asn Leu Glu Thr
1               5

<210> SEQ ID NO 42
<211> LENGTH: 9
```

```
<212> TYPE: PRT
<213> ORGANISM: Artificial Sequence
<220> FEATURE:
<223> OTHER INFORMATION: 64-31 CDR-L3

<400> SEQUENCE: 42

Gln Gln Ala Thr Gly Trp Pro Phe Thr
1               5

<210> SEQ ID NO 43
<211> LENGTH: 6
<212> TYPE: PRT
<213> ORGANISM: Artificial Sequence
<220> FEATURE:
<223> OTHER INFORMATION: 64-32 CDR-H1

<400> SEQUENCE: 43

Ser Lys Tyr Ala Met His
1               5

<210> SEQ ID NO 44
<211> LENGTH: 10
<212> TYPE: PRT
<213> ORGANISM: Artificial Sequence
<220> FEATURE:
<223> OTHER INFORMATION: 64-32 CDR-H2

<400> SEQUENCE: 44

Ala Ile Ser Gly Ser Gly Gly Tyr Thr Tyr
1               5                   10

<210> SEQ ID NO 45
<211> LENGTH: 11
<212> TYPE: PRT
<213> ORGANISM: Artificial Sequence
<220> FEATURE:
<223> OTHER INFORMATION: 64-32 CDR-H3

<400> SEQUENCE: 45

Asp Leu Asp Phe Arg Ile Val Gly Phe Asp Val
1               5                   10

<210> SEQ ID NO 46
<211> LENGTH: 11
<212> TYPE: PRT
<213> ORGANISM: Artificial Sequence
<220> FEATURE:
<223> OTHER INFORMATION: 64-32 CDR-L1

<400> SEQUENCE: 46

Gln Ala Ser Gln Asp Ile Ser Asn Tyr Leu Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: 64-32 CDR-L2

<400> SEQUENCE: 47

Asp Ala Ser Asn Leu Glu Thr
1               5

<210> SEQ ID NO 48
<211> LENGTH: 9
<212> TYPE: PRT
```

```
<213> ORGANISM: Artificial Sequence
<220> FEATURE:
<223> OTHER INFORMATION: 64-32 CDR-L3

<400> SEQUENCE: 48

Gln Gln Phe Asn Thr Val Pro Leu Thr
1               5

<210> SEQ ID NO 49
<211> LENGTH: 6
<212> TYPE: PRT
<213> ORGANISM: Artificial Sequence
<220> FEATURE:
<223> OTHER INFORMATION: 64-39 CDR-H1

<400> SEQUENCE: 49

Ser Arg Tyr Ala Met His
1               5

<210> SEQ ID NO 50
<211> LENGTH: 10
<212> TYPE: PRT
<213> ORGANISM: Artificial Sequence
<220> FEATURE:
<223> OTHER INFORMATION: 64-39 CDR-H2

<400> SEQUENCE: 50

Gly Ile Ser Gly Ser Gly Gly Gly Thr Tyr
1               5                   10

<210> SEQ ID NO 51
<211> LENGTH: 11
<212> TYPE: PRT
<213> ORGANISM: Artificial Sequence
<220> FEATURE:
<223> OTHER INFORMATION: 64-39 CDR-H3

<400> SEQUENCE: 51

Asp Leu Asp Tyr Arg Val Ser Gly Phe Asp Val
1               5                   10

<210> SEQ ID NO 52
<211> LENGTH: 11
<212> TYPE: PRT
<213> ORGANISM: Artificial Sequence
<220> FEATURE:
<223> OTHER INFORMATION: 64-39 CDR-L1

<400> SEQUENCE: 52

Gln Ala Ser Gln Asp Ile Ser Asn Tyr Leu Asn
1               5                   10

<210> SEQ ID NO 53
<211> LENGTH: 7
<212> TYPE: PRT
<213> ORGANISM: Artificial Sequence
<220> FEATURE:
<223> OTHER INFORMATION: 64-39 CDR-L2

<400> SEQUENCE: 53

Asp Ala Ser Asn Leu Glu Thr
1               5

<210> SEQ ID NO 54
<211> LENGTH: 9
<212> TYPE: PRT
<213> ORGANISM: Artificial Sequence
```

```
<220> FEATURE:
<223> OTHER INFORMATION: 64-39 CDR-L3

<400> SEQUENCE: 54

Gln Gln Phe Tyr Ser Val Pro Leu Thr
1               5

<210> SEQ ID NO 55
<211> LENGTH: 6
<212> TYPE: PRT
<213> ORGANISM: Artificial Sequence
<220> FEATURE:
<223> OTHER INFORMATION: 66-6 CDR-H1

<400> SEQUENCE: 55

Ser Lys Tyr Ala Met His
1               5

<210> SEQ ID NO 56
<211> LENGTH: 10
<212> TYPE: PRT
<213> ORGANISM: Artificial Sequence
<220> FEATURE:
<223> OTHER INFORMATION: 66-6 CDR-H2

<400> SEQUENCE: 56

Ala Ile Ser Gly Ser Gly Gly Ser Thr Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: 66-6 CDR-H3

<400> SEQUENCE: 57

Asp Leu Asp Tyr Arg Phe Ser Gly Phe Asp Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: 66-6 CDR-L1

<400> SEQUENCE: 58

Gln Ala Ser Gln Asp Ile Ser Asn Tyr Leu Asn
1               5                   10

<210> SEQ ID NO 59
<211> LENGTH: 7
<212> TYPE: PRT
<213> ORGANISM: Artificial Sequence
<220> FEATURE:
<223> OTHER INFORMATION: 66-6 CDR-L2

<400> SEQUENCE: 59

Asp Ala Ser Asn Leu Glu Thr
1               5

<210> SEQ ID NO 60
<211> LENGTH: 9
<212> TYPE: PRT
<213> ORGANISM: Artificial Sequence
<220> FEATURE:
```

```
<223> OTHER INFORMATION: 66-6 CDR-L3

<400> SEQUENCE: 60

Gln Gln Phe Ala Ala Ile Pro Leu Thr
1               5
```